US008692035B2

(12) United States Patent
Berretta

(10) Patent No.: US 8,692,035 B2
(45) Date of Patent: Apr. 8, 2014

(54) ADIABATIC PROCESS FOR MAKING MONONITROBENZENE

(75) Inventor: Sergio Berretta, Vancouver (CA)

(73) Assignee: Noram International Limited (IE)

( * ) Notice: Subject to any disclaimer, the term of this patent is extended or adjusted under 35 U.S.C. 154(b) by 399 days.

(21) Appl. No.: 13/128,595

(22) PCT Filed: Nov. 10, 2008

(86) PCT No.: PCT/CA2008/001959
§ 371 (c)(1),
(2), (4) Date: Jun. 7, 2011

(87) PCT Pub. No.: WO2010/051616
PCT Pub. Date: May 14, 2010

(65) Prior Publication Data
US 2011/0245547 A1    Oct. 6, 2011

(51) Int. Cl.
*C07C 205/00*    (2006.01)
(52) U.S. Cl.
USPC .......................................... 568/939; 568/927
(58) Field of Classification Search
None
See application file for complete search history.

(56) References Cited

U.S. PATENT DOCUMENTS

| | | |
|---|---|---|
| 2,256,999 A | 9/1941 | Castner |
| 4,021,498 A | 5/1977 | Alexanderson et al. |
| 4,091,042 A | 5/1978 | Alexanderson et al. |
| 5,313,009 A | 5/1994 | Guenkel et al. |
| 6,242,657 B1 | 6/2001 | Konig et al. |

FOREIGN PATENT DOCUMENTS

| | | |
|---|---|---|
| CA | 2 308 288 A1 | 5/1999 |
| CN | 1054247 | 2/1990 |

OTHER PUBLICATIONS

Quadros, Paulo A. et al., "Continuous adiabatic industrial benzene nitration with mixed acid at a pilot plant scale", Chemical Engineering Journal 108, (2005) 1-11.
Quadros, Paulo A. et al., "Different Modeling Approaches for a Heterogeneous Liquid-Liquid Reaction Process", Ind. Eng. Chem. Res. 2005, 44, 9414-9421.
Quadros, Paulo A. et al., "Nitrophenols Reduction in the Benzene Adiabatic nitration Process", Ind. Eng. Chem. Res. 2004, 43, 4438-4445.

*Primary Examiner* — Sudhakar Katakam
(74) *Attorney, Agent, or Firm* — McKee, Voorhees & Sease, P.L.C.

(57) ABSTRACT

An adiabatic process for making mononitrobenzene by the nitration of benzene which minimizes the formation of nitrophenols and dinitrobenzene by-products. The process uses a mixed acid having less than 3 wt % nitric acid, 55 to 80 wt % sulfuric acid, and water. The initial temperature of the mixed acid is in the range of 60 to 96° C. The nitration reaction is complete in about 300 seconds and produces less than 1,200 ppm nitrophenols and less than about 80 ppm dinitrobenzene. The reaction can be carried out in a plug-flow or a stirred pot reactor, or a combination of such reactors.

19 Claims, 1 Drawing Sheet

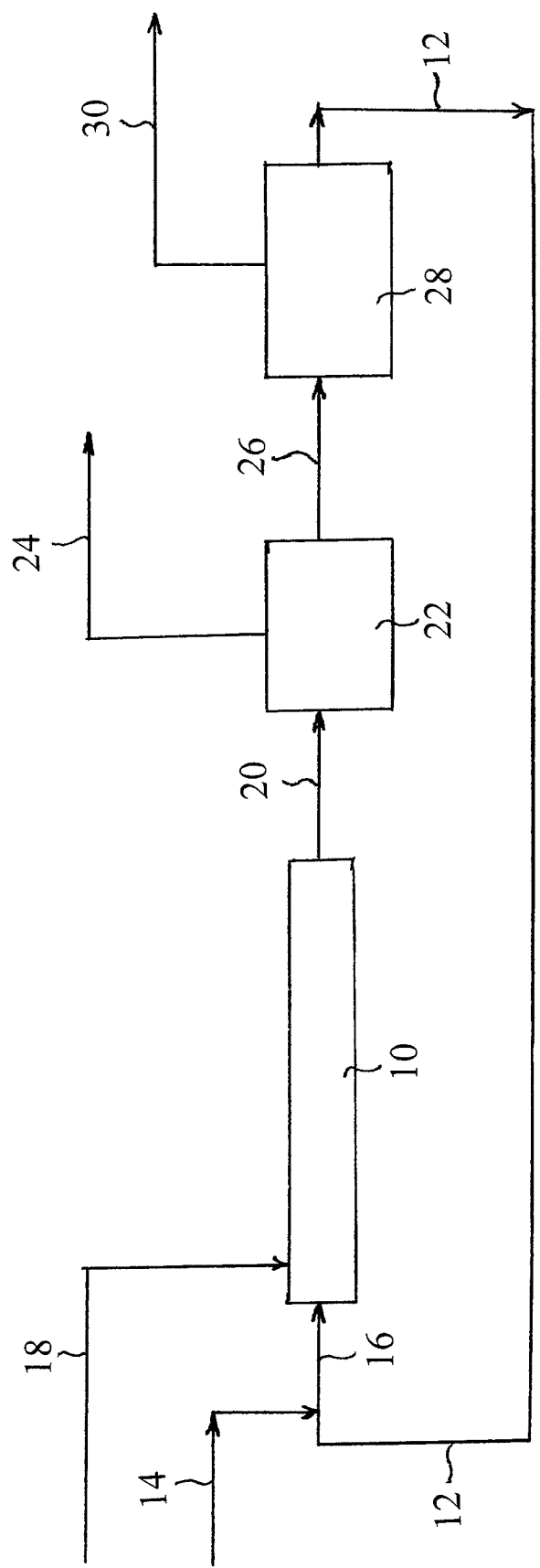

ADIABATIC PROCESS FOR MAKING MONONITROBENZENE

CROSS-REFERENCE TO RELATED APPLICATIONS

This is a National Phase application claiming priority to PCT/CA2008/001959 filed Nov. 10, 2008, herein incorporated by reference in its entirety.

TECHNICAL FIELD OF THE INVENTION

The invention relates to an improved process for the manufacture of mononitrobenzene. More particularly, it relates to an adiabatic nitration process which minimizes the formation of undesired by-products.

BACKGROUND OF THE INVENTION

Mononitrobenzene is produced industrially using a number of adiabatic nitration technologies. Adiabatic nitration was first introduced by Castner, as described in U.S. Pat. No. 2,256,999. Adiabatic nitration of benzene has replaced the previously-used energy-intensive isothermal nitration process.

In the late 1970's Alexanderson et al. proposed changes to the composition and temperature limits of Castner's adiabatic nitration process, leading to a commercially useful process, described in U.S. Pat. Nos. 4,021,498 and 4,091,042. U.S. Pat. No. 4,021,498 describes a process for making mononitrobenzene using a mixed acid having a nitric acid strength of 5 to 8.5 wt %, a sulfuric acid strength of 60 to 70 wt %, and not less than 25% water, the initial reactant temperature being in the range of 40 to 80° C. U.S. Pat. No. 4,091,042 describes an improved process using a mixed acid having a nitric acid strength of 3 to 7.5 wt %, a sulfuric acid strength of 58.5 to 66.5 wt %, and the balance water. The temperature of the initial mixed acid is in the range of 80 to 120° C. Compared with the prior art isothermal technology these conditions led to a reduction in the production of the by-product dinitrobenzene, stated as less than 500 ppm in the '042 patent. However, the conditions described in the Alexanderson et al. patents still produce a high level of by-product nitrophenols.

Since the 1990's, most new industrial mononitrobenzene adiabatic plants have been built based on process conditions described by Guenkel et al. in U.S. Pat. No. 5,313,009. Guenkel et al. proposed a new set of conditions to nitrate benzene which reduced formation of oxidation by-products (i.e., nitrophenols) below prior art levels. In the Guenkel et al. process the initial mixed acid temperature must be in the range of 97° C. and 120° C. Reaction rates are stated to maintained high by keeping the reactor inlet mixed acid temperature high (i.e., above 97° C.) and by maintaining the sulfuric acid strength relatively high. The by-product nitrophenol formation for the conditions described by Guenkel et al. is in the order of 1700 ppm. Experiments have shown that the by-product dinitrobenzene formation under the conditions described by Guenkel et al. is in the range of 250 to 300 ppm.

Nitrophenols and dinitrobenzene are the main impurities formed in the industrial production of mononitrobenzene. Reducing the levels of these impurities is a very important goal in the art. Most industrially-produced mononitrobenzene is used in the production of aniline, and these impurities are believed to be the main compounds negatively affecting catalyst life in the downstream aniline process. The operating cost and capital investment required to remove and treat these by-products is significant.

SUMMARY OF THE INVENTION

The present invention provides a process for the production of mononitrobenzene that significantly reduces the formation of nitrophenol and dinitrobenzene by-products, over the prior art processes, while maintaining an acceptably high reaction rate.

Accordingly, the invention provides a continuous adiabatic process for the mononitration of benzene, comprising the steps of providing in a reactor benzene and mixed acid, the mixed acid comprising less than 3 wt % nitric acid, 55 to 80 wt % sulfuric acid, and water, the mixed acid having an initial temperature in the range of 60° C. to 96° C.; and allowing the benzene and mixed acid to react to produce a composition comprising mononitrobenzene. The process produces less than about 1,500 ppm nitrophenols and less than about 100 ppm dinitrobenzene, alternatively less than 1,200 ppm nitrophenols and less than 50 ppm dinitrobenzene.

BRIEF DESCRIPTION OF THE DRAWING

FIG. 1 is a flow chart of the process of mononitration using a plug-flow nitrator, according to one embodiment of the invention.

DETAILED DESCRIPTION OF THE PREFERRED EMBODIMENTS

In general terms, the process comprises preparing a mixture of nitric acid, sulfuric acid and water, referred to as "mixed acid," feeding it into a reactor, feeding benzene into the reactor, allowing the mixed acid and benzene to react under conditions where it is either continually or periodically mixed, to produce mononitrobenzene, and separating the mononitrobenzene from the spend acid. The concentration and temperature of the reactants are carefully controlled to achieve the desired results, as described below.

The nitration process can be carried out in a number of reactor types arrangements, for example but not limited to: plug flow reactors, one or more stirred pot reactor in series, or a combination of plug flow reactors and stirred pot (one or more) reactors. The stirred pot reactors can be continuously or intermittently agitated. For the purpose of illustration, the plug flow reactor process, shown in FIG. 1, is described.

A plug flow nitration reactor 10 receives a stream of reconcentrated sulfuric acid from a conduit 12 and a stream of nitric acid from a conduit 14. The two acid flows are mixed in a conduit 16 prior to entering the nitrator. The reactant stream of mixed acid in conduit 16 entering the nitrator comprises nitric acid, sulfuric acid and water. The concentration of nitric acid in the mixed acid is less than 3 wt %, alternately about 2.0 to 2.9 wt %, alternately about 2.2 wt %. The concentration of sulfuric acid in the mixed acid is 55 to 80 wt %, alternately about 60 to 73 wt %, alternately about 65 wt %. The balance of the mixed acid is water, which comes partly from the nitric acid stream and partly from the reconcentrated sulfuric acid stream. The mixed acid stream is fed into the nitrator 10. The temperature of the mixed acid stream is in the range of 60 to 96° C., alternately in the range of 70 to 90° C., alternately about 80° C. A reactant stream of benzene is fed from a conduit 18, where it mixes with the mixed acid. The benzene is fed in a stoichiometric excess of 5 to 15%, alternatively 6 to 8%, relative to the nitric acid. The benzene can be fed at room
} temperature or it can be pre-heated to achieve energy savings in the operation of the process.

It is not necessary that the mixed acid be formed before entry into the nitrator: the nitric and sulfuric acids can be fed separately into the nitrator, forming the mixed acid within the nitrator.

The benzene and mixed acid are allowed to react while moving through the nitrator, under conditions where it is continually or periodically mixed, until the reaction is complete, which takes about 300 seconds.

One mode of operation of the process is to run with a mixed acid temperature of 80° C. or lower. Given that benzene boils at 80.1° C. at atmospheric conditions, the suggested mode of operation has the additional advantage of allowing the process running at essentially atmospheric pressure through the length of the reactor.

The reaction fluids exit the nitrator and pass via a conduit 20 to a separator 22. Here, product mononitrobenzene is separated from the spent acid, the mononitrobenzene being removed via a conduit 24 and the spent acid passing via conduit 26 to a sulfuric acid concentrator 28.

Water is removed from the concentrator via conduit 30 and reconcentrated sulfuric acid is circulated via conduit 12 to the nitrator 10.

For the adiabatic process of the invention, the reactor average temperature, which it is believed to highly affect by-product formation, is determined by the initial mixed acid temperature and the concentration of nitric acid in the mixed acid. The inventor believes that as a practical matter the nitric acid strength in the mixed acid should be maintained as low as possible to limit the temperature rise through the reactor and improve the feed conversion efficiency of the reactor. It is believed that higher conversion rates are better obtained at low nitric acid strength in the mixed acid due to the following effects. At low nitric acid strengths, the benzene mass flow, which is proportional to the nitric acid mass flow, remains low relative to the mixed acid flow, which improves the ability to disperse the benzene phase and reduces the rate of coalescing of the benzene phase, both of which improve reactor efficiency. In addition, at these conditions there is an increase in the dissociation of the nitric acid to nitronium ion. As a result of the desired low nitric acid strengths in the mixed acid, the effect of the nitric acid strength on temperature rise through the reactor is modest. Hence, it is the initial mixed acid temperature that has the greatest influence on the average reaction temperature.

The desired conditions for the nitration reaction of the invention are thus a low initial mixed acid temperature, a nitric acid concentration in the mixed acid below 3 wt %, and relatively low sulfuric acid strength in the mixed acid. These conditions would be expected to produce very low reaction rates. However, the inventor has determined that under these conditions the reaction rates are sufficiently high to be used in a practical commercial process. The specified process conditions lead to a nitrophenol reduction of almost 50% and a simultaneous drop of about an order of magnitude in formation of dinitrobenzene relative to the levels produced by the process of Guenkel et al., U.S. Pat. No. 5,313,009. Using the process of the invention, the formation of nitrophenol by-product is less than 1,500 ppm, preferably less than 1,200 ppm, more preferably less than 1,000 ppm; and the formation of dinitrobenzene by-product is less than 100 ppm, preferably less than 80 ppm, and more preferably less than 50 ppm.

Under the specified process conditions full conversion of the reactants is obtained in approximately 300 seconds. This is a surprisingly fast reaction rate. Without being bound by a particular theory, it is believed that the fast reaction time under these conditions may be due to the heterogenous nature of the reaction. The homogeneous benzene nitration rate constant is known to decrease rapidly with lower temperature and lower acid strength (see, for example: N. C. Marziano, A. Tomasin, C. Tortato and J. M. Zaldivar, "Thermodynamic nitration rates of aromatic compounds. Part 4. Temperature dependence in sulfuric acid of HNO3-NO2+ equilibrium, nitration rates and acidic properties of the solvent", J. Chem. Soc., Perkin Trans. 2 (1998) 1973-82), leading to an expectation of unacceptably long reaction times at low acid strength and temperature. However, the industrial reaction is run under conditions where the benzene is present as a second phase. For such a two-phase reaction, the rate is also influenced by the ability to move reactants between phases and their reactivities in the phases. Because of this, the overall rate can be influenced by many factors other than the simple nitration rate constant. These factors include: the solubilities of the different reacting components in the two phases, their activity coefficients in the phases, and their diffusion coefficients. The reaction is also influenced by the interfacial area between the two phases, which is in turn affected by surface tension, the degree of inter-miscibility of the two phases, and the viscosities and densities of the phases. Finally, the industrial mixed acid properties will differ from those reported in the literature because of the presence of dissolved organic compounds (mainly benzene and mononitrobenzene) and the higher nitric acid strengths typically used. All of these factors interact with each other and are influenced by temperature and the mixed acid composition and it is thought that some combination of these factors may be behind the results disclosed herein.

The findings indicate that for a commercially acceptable increase in reactor size, a very significant decrease in by-products is achieved.

EXAMPLE

Eight batch nitrations were carried out in an insulated, continuously stirred reactor. From chemical reactor theory, the reaction with time in a batch stirred reactor is approximately equivalent to a reaction with distance in an ideal continuously mixed plug flow reactor. Therefore the results from these batch stirred reactor experiments more closely represent the results for an ideal plug flow nitration reactor than a CSTR reactor. All experiments were made with the same concentration of nitric acid in the mixed acid, which was less than 3 wt % nitric acid, and the same sulfuric acid strength in the mixed acid. Only the initial mixed acid temperature, i.e. the temperature prior to commencement of the nitration reaction, was varied, leading to different average reaction temperatures. At the start of each experiment, sulfuric acid and nitric acid were well mixed in the reactor at a controlled initial temperature. An appropriate amount of benzene was then added to initiate the reaction. Since the amount of heat released in the reaction was always the same, the temperature rise was always the same, so the average temperature was a direct reflection of the starting temperature.

Table 1 shows the effect of temperature on nitrophenol formation in the eight tests. Within the experimental limits, the data show that nitrophenol formation doubles for every 20 to 25° C. of temperature increase. Hence, it is advantageous to start the reaction with the lowest mixed acid temperature possible. This contrasts with the teaching in U.S. Pat. No. 5,313,009 Guenkel et al. that the process should start with the highest reasonable mixed acid temperature.

TABLE 1

Effect of Initial Mixed Acid Temperature on Nitrophenol Formation

| Test No. | Initial Mixed Acid Temperature* (° C.) | Nitric Acid Concentration in Initial Mixed Acid (wt %) | Sulfuric Acid Concentration in Initial Mixed Acid (wt %) | Reaction Excess Benzene (wt %) | Total Nitrophenol Formation** (ppm - wt) |
|---|---|---|---|---|---|
| 1 | 57 | 2.85 | 67 | 12 | 426 |
| 2 | 58 | 2.85 | 67 | 12 | 431 |
| 3 | 79 | 2.85 | 67 | 12 | 725 |
| 4 | 79 | 2.85 | 67 | 12 | 676 |
| 5 | 98 | 2.85 | 67 | 12 | 1,181 |
| 6 | 99 | 2.85 | 67 | 12 | 1,051 |
| 7 | 108 | 2.85 | 67 | 12 | 1,641 |
| 8 | 109 | 2.85 | 67 | 12 | 1,630 |

*Reactor temperature increases through experiments were approximately 20° C.
**Typical split of nitrophenol species is approximately 86% dinitrophenol species, 7% mononitrophenol species, and 7% picric acid.

For Test Nos. 3 and 4, in which the initial mixed acid temperature was 79° C., the level of nitrophenols formed was 725 and 676 ppm respectively. The dinitrobenzene levels were not measured; however, based on other plant trials conducted it is determined that the formation of dinitrobenzene in these Tests was well below 50 ppm.

Although the invention has been described in terms of various embodiments, it is not intended that the invention be limited to these embodiments. Various modifications within the scope of the invention will be apparent to those skilled in the art. The scope of the invention is defined by the claims that follow.

What is claimed is:

1. An adiabatic process for the mononitration of benzene, comprising the steps of:

providing in a reactor benzene and a mixed acid, the mixed acid comprising less than 3 wt % nitric acid, 55 to 80 wt % sulfuric acid, and water, the mixed acid having an initial temperature in the range of 60° C. to 96° C., the benzene being provided in a stoichiometric excess of 5 to 15% relative to the nitric acid; and allowing the benzene and the mixed acid to react to produce a composition comprising mononitrobenzene.

2. A process according to claim 1, wherein the process causes the formation of less than 1,500 ppm nitrophenols.

3. A process according to claim 1, wherein the process causes the formation of less than 1,200 ppm nitrophenols.

4. A process according to claim 1, wherein the process causes the formation of less than 1,000 ppm nitrophenols.

5. A process according to claim 1, wherein the process causes the formation of less than 100 ppm dinitrobenzene.

6. A process according to claim 1, wherein the process causes the formation of less than 80 ppm dinitrobenzene.

7. A process according to claim 1, wherein the process causes the formation of less than 50 ppm dinitrobenzene.

8. A process according to claim 1, wherein the mixed acid comprises 2.0 to 2.9 wt % nitric acid.

9. A process according to claim 1, wherein the mixed acid comprises 2.0 to 2.4 wt % nitric acid.

10. A process according to claim 1, wherein the mixed acid comprises 60 to 73 wt % sulfuric acid.

11. A process according to claim 1, wherein the initial temperature of the mixed acid is in the range of 70 to 90° C.

12. A process according to claim 1, wherein the initial temperature of the mixed acid is in the range of 80 to 90° C.

13. A process according to claim 1, wherein the initial temperature of the mixed acid is in the range of 60° C. to 80° C.

14. A process according to claim 13, wherein the process runs at substantially atmospheric pressure.

15. A process according to claim 1, wherein the benzene comprises a stoichiometric excess of 6 to 8% relative to the nitric acid.

16. A process according to claim 1, wherein the reactor is a plug flow nitrator.

17. A process according to claim 1, wherein the reactor comprises one or more stirred pot reactors in series.

18. A process according to claim 1, wherein the reactor comprises a combination of one or more plug flow reactors and one or a series of stirred pot reactors.

19. A process according to claim 1, wherein the benzene and the mixed acid are each introduced into the reactor as a respective reactant stream.

* * * * *